US006689793B2

(12) United States Patent
Uckun et al.

(10) Patent No.: US 6,689,793 B2
(45) Date of Patent: *Feb. 10, 2004

(54) PIPERIDINYLETHYL-, PHENOXYETHYL-, AND β-FLUOROPHENETHYL-SUBSTITUTED THIOUREA COMPOUNDS WITH POTENT ANTI-HIV ACTIVITY

(75) Inventors: Fatih M. Uckun, White Bear Lake, MN (US); Taracad K. Venkatachalam, Maplewood, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/006,300

(22) Filed: Dec. 6, 2001

(65) Prior Publication Data

US 2002/0151568 A1 Oct. 17, 2002

Related U.S. Application Data

(60) Provisional application No. 60/251,716, filed on Dec. 6, 2000.

(51) Int. Cl.$^7$ ..................... A61K 31/445; C07D 401/02
(52) U.S. Cl. ...................................... 514/318; 546/194
(58) Field of Search ........................... 514/318; 546/193

(56) References Cited

U.S. PATENT DOCUMENTS

| | | | |
|---|---|---|---|
| 5,593,993 A | 1/1997 | Morin, Jr. et al. | 514/247 |
| 5,658,907 A | 8/1997 | Morin, Jr. et al. | 514/247 |
| 5,686,428 A | 11/1997 | Eriksson et al. | 514/50 |
| 5,714,503 A | 2/1998 | Morin, Jr. et al. | 514/332 |
| 5,786,462 A | 7/1998 | Schneider et al. | 536/23.1 |
| 5,998,411 A | * 12/1999 | Vig et al. | 514/235.5 |
| 6,300,351 B1 | 10/2001 | Vig et al. | 514/353 |
| 6,380,190 B1 | * 4/2002 | Vig et al. | 514/235.5 |

FOREIGN PATENT DOCUMENTS

| | | |
|---|---|---|
| EP | 0 420 763 A2 | 4/1991 |
| JP | 07025770 | 1/1995 |
| WO | WO 93/03022 | 2/1993 |
| WO | WO 95/06034 | 3/1995 |
| WO | WO 99/47501 | 9/1999 |

OTHER PUBLICATIONS

Venkatachalam et al. "Piperidinylethyl . . . " CA 134:202425 (2001).*
Ahgren, C., et al., 1995, *Antimicrob. Agents Chemotherapy*, 39, 1329–1335 The PETT Series, a New Class of Potent Nonnucleoside Inhibitors of Human Immunodeficiency Virus Type 1 Reverse Transcriptase.
Baba, M., et al., 1992, *Antiviral Res.*, 17, 245–264 Highly Potent and selective inhibition of HIV–1 replication by 6–phenylthiouracil derivatives.
Baba, M., et al., 1992, *Antiviral Res.*, 17, 245–264 A Multidisciplinary Journal of Antiviral Agents, Natural Host Defense Mechanisms, Interferons and Antiviral Vaccines.
Balzarini, J. et al., 1992, *Proc. Natl. Acad. Sci. U S A*, 89, 4392–4396
2',5'–Bis–O–(*tert*–butyldimethylsilyl)–3'–spiro–5"–(4"–amino–1",2"–oxathiole–2",2"–dioxide)pyrimidine (TSAO) nucleoside analogues: Hightly selective inhibitors of human immunodeficiency virus type 1 that are targeted at the viral reverse transcriptase.
Bartlett, P.A. et al., 1989, *Molecular Recognition in Chemical and Biological Problems*, Special Pub., Royal Chem. Soc., 78, 182–196 Caveat: A Program to Facilitate the Structure–derived Design of Biologically Active Molecules.
Bell, F. W., et al., 1995, *J. Med. Chem.*, 38, 4929–4936 Penethylthiazolethiourea (PETT) Compounds, a New Class of HIV–1 Reverse Transcriptase Inhibitors. 1. Syntheis and Basic Structure–Activity Relationship Studies of PETT Analogs.
Blaney, J.M. and Dixon, J.S., 1993, *Perspectives in Drug Discovery and Design*, 1, 301 A good ligand is hard to find: Automated docking methods.
Bohm, H. J., 1992, *J. Comput. Aided. Mol. Des.*, 6, 593–606 LUDI: rule–based automatic design of new substituents for enzyme inhibitor leads.
Bohm, H.J., 1992, *J. Comp. Aid. Molec. Design*, 6, 61–78 The computer program LUDI: A new method for the de novo design of enzyme inhibitors.
Bohm, H. J., *J. Comput. Aided. Mol. Des.*, 1992, 8, 243–256; 1996 The development of a simple empirical scoring function to estimate the binding constant for a protein–ligand complex of known three–dimensional structure.
Bosworth, N., et al., 1989, *Nature*, 341:167–168 Scintillation proximity assay.
Brooks, B.R. et al., 1983, *J. Comp. Chem.*, 4, 187–217 CHARMM: A Program for Macromolecular Energy, Minimization, and Dynamics Calculations.
Burkert, U. and Allinger, N.L., 1982, Molecular Mechanics, *ACS Monograph*, 177, 59–78, American Chemical Society, D.C. Methods for the Computation of Molecular Geometry.
Cantrell, A. S., et al., 1996, *J. Med. Chem.*, 39, 4261–4274 Phenethylthiazolylthiourea (PETT) Compounds as a New Class of HIV–1 Reverse Transcriptase Inhibitors. 2. Synthesis and Further Structure–Activity Relationship Studies of PETT Analogs.

(List continued on next page.)

*Primary Examiner*—Ceila Chang
(74) *Attorney, Agent, or Firm*—Merchant & Gould P.C.

(57) ABSTRACT

The present invention is directed to derivatives of piperidinylethyl, phenoxyethyl, and fluorophenethyl bromopyridyl thioureas, which have been found to be effective non-nucleoside inhibitors (NNRTI) of NNI-resistant and multi-drug resistant human immunodeficiency virus (HIV)-1 reverse transcriptase (RT). The present invention is further directed to methods of using the above derivatives to treat patients with NNI-resistant or multi-drug resistant human immunodeficiency virus (HIV)-1.

13 Claims, No Drawings

OTHER PUBLICATIONS

Chemical substance index page, *Chemical Abstracts, 13th Collective Chemical Substance Index*, Book 52, p. 1272 (1992–1996).

Connolly, M. L., 1983, *Science*, 221, 709–713 Solvent–Accessible Surfaces of Proteins and Nucleic Acids.

Danel, K., et al., 1996, *J. Med. Chem., 39*, 2427–2431 Synthesis and Potent Anti–HIV–1 Activity of Novel 6–Benzyluracil Analogues of 1–[2–Hydroxyethoxy) methyl]–6–(phenylthio)thymine.

Danel, K. et al., 1997, *Acta Chemica Scandinavica, 51*, 426–430 Anti–HIV Active Napthyl Analogues of HEPT and DABO.

Danel, K. et al., 1998, *J. Med. Chem., 41*, 191–198 Synthesis and Anti–HIV–1 Activity of Novel 2,3–Dihydro–7H–thiazolo[3,2–α]pyrimidin–7–ones.

Das, K. et al., 1996, *J. Mol. Biol., 264*, 1085–1100 Crystal Structures of 8–Cl and 9–Cl TIBO Complexed with Wild–type HIV–1 RT and 8–Cl TIBO Complexed with the Tyr181Cys HIV–1 RT Drug–resistant Mutant.

Davies et al., "Condensed Thiophen Ring Systems. Part XIX. Synthesis of 6,7–Dhydrothieno [3,2–c] pyridines and 4,5–Dihydrothieno [2,3–c] pridines by Intramolecular Cyclisation of 2–(2– or 3–Thienyl)ethyl Isothiocyanate", *J.C.S. Perkin I*, pp. 138–141 (1976).

D–Cruz, O. et al., "Novel Thiourea Compounds As Dual–Function Microbicides", *Chemical Abstract*, Abstract No. 133:159648d, vol. 133, No. 12, 1 page (2000).

De Clerq, E., 1992, *J. Acquired Immune Defic. Syndr. Res. Human. Retrovirus, 8*, 119–134.

Deeks et al., 1997, *JAMA*, vol. 277, No. 2 HIV–1 Protease Inhibitors.

Ding, J., 1995, et al., *Nat. Struct. Biol.*, 2, 407–415 Structure of HIV–1 RT/TIBO R 86183 complex reveals similarity in the binding of diverse nonnucleoside inhibitors.

Erice, A. et al., 1993, *Antimicrob. Ag. Chemother., 37*, 835 Anti–Human Immunodeficiency Virus Tyoe 1 Activity of an Anti–CD4 Immunoconjugate Containing Pokeweed Antiviral Protein.

Gittos et al., "A New Synthesis of Isocyanates", *J.C.S. Perkin I*, pp. 141–143 (1976).

Goodsell, D.S. and Olson, A.J., 1990, *Proteins: Struct. Funct. Genet., 8*, 195–202 Automated Docking of Substrates to Proteins by Simulated Annealing.

Greene, W. C., 1991, *New England Journal of Medicine, 324*, 308–317 The Molecular Biology of Human Immunodeficiency Virus Type 1 Infection.

Hopkins, A. L. et al., 1996, *J. Med. Chem., 39*, 1589–1600 Complexes of HIV–1 Reverse Transcriptase with Inhibitors of the HEPT Series Reveal Conformational Changes Relevant to the Design of Potent Non–Nucleoside Inhibitors.

Jones, T. A. et al., 1991, *Acta Crystallogr. A., 47*, 110–119 Improved Methods for Building Protein Models in Electron Denisty Maps and the Location of Errors in these Models.

Kohlstaedt, L. A. et al., 1992, *Science, 256*, 1783–1790 Crystal Structure at 3.5 Å Resolution of HIV–1 Reverse Transcriptase Complexed with an Inhibitor.

Kuntz, I.D., et al., 1995, *J. Mol. Biol.*, 1982, 161, 269–288 A Geometric Approach to Macromolecule–Ligand Interactions.

Luty, B. A. et al., 1995, *J. Comp. Chem., 16*, 454–464 A Molecular Mechanics/Grid Methods for Evaluation of Ligand–Receptor Interactions.

Mai, A. et al., 1997, *J. Med. Chem., 40*, 1447–1454 Dihydro(alkylthio)(naphthylmethyl)oxopyrimidines: Novel Non–Nucleoside Reverse Transcriptase Indhibitors of the S–DABO Series.

Mao, C. et al., "Structure–Based Design of N–[2–(1–Piperidinylethyl)]–N'–[2–(5–Bromopyridyl)]–Thiourea and N–2–(1–Piperazinylethyl)–N'–[2–(5–Bromopyridyl)]–Thiourea as Potent Non–Nucleoside Inhibitors of HIV–1 Reverse Transcriptase", *Bioorganic & Medicinal Chemistry Letters 8*, pp. 2213–2218 (1998).

Mao, C. et al., "Rational Design Of N–[2–2,5–Dimethoxyphenylethyl)]–N'[2–(5—Bromopyridyl)]–Thiourea (HI–236) As A Potent Non–Nucleoside Inhibitor Of Drug–Resistant Human Immunodeficiency Virus", *Bioorganic & Medicinal Chemistry Letters*, vol. 9, pp. 1593–1598 (1999).

Marshall, GR., 1987, *Ann. Ref. Pharmacol. Toxicol., 27*, 193 Computer–Aided Drug Design.

Martin, Y.C., 1992, *J. Med. Chem., 35*, 2145–2154 3D Database Searching in Drug Design.

Mitsuya, H. et al., 1990, *Science, 249*, 1533–1544 Molecular Targets for AIDS Therapy.

Nishibata, Y. and Itai, A., 1991, *Tetrahedron, 47*, 8985 Automatic Creation of Drug Candidate Structures Based on Receptor Structure. Starting Point for Artificial Lead Generation.

Pauwels, R. et al., 1990, *Nature, 343*, 470–474 Potent and selective inhibitionof HIV–1 replication in vitro by a novel series of TIBO derivatives.

Pontikis, R. et al., 1997, *J. Med. Chem., 40*, 1845–1854 Synthesis and Anti–HIV Activity of Novel N–1 Side Chain–Modified Analogs of 1–[(2–Hydroxyethoxy) methyl]–6–(phenylthio)thymine (HEPT).

Remington's Pharmaceutical Sciences, Chapter 43, 14th Ed., Mack Publishing Col, Easton PA 18042, USA Topical Drugs (1965).

Ren, J. et al., 1995, *Structure, 3*, 915–926 The Structure of HIV–1 reverse transcriptase complexed with 9–chloro–TIBO: lessons for inhibitor design.

Romero, D. L. et al., 1993, *J. Med. Chem., 36*, 1505–1508 Bis(heteroaryl)piperazine (BHAP) Reverse Transcriptase Inhibitors: Structure–Activity Relationships of Novel Substituted Indole Analogues and the Identification of 1–[(5–Methanesulfonamido–1H–indol–2–yl)–carbonyl]–4–[3–[(1–methylethyl)amino]–pyridinyl]piperazine Monomethanesulfonate (U–90152S), a Second–Generation Clinical Candidate.

Sahlberg, et al., 1998, *Bioorganic & Medicinal Chemistry Letters 8*, pp. 1511–1516 "Synthesis and Anti–HIV Activities of Urea–PETT Analogs Belonging to a New Class of Potent Non–Nonucleoside HIV–1 Reverse Transcriptase Inhibitors".

Smith et al., 1995, *Protein Science* 4:2203–222 Molecular modeling studies of HIV–1 reverse transcriptase nonnucleoside inhibitors: Total energy of complexation as a predictor of drug placement and activity.

Sudbeck, E. A. et al., 1998, *Antimicrobial Agents and Chemotherapy*, 42(12), 3225–33 Structure–Based Design of Novel Dihydroalkoxybenzyloxopyrimidine Derivatives as Potent Nonnucleoside Inhibitors of the Human Immunodeficiency Virus Reverse Transcriptase.

Tanaka, H. et al., 1991, *J. Med. Chem., 34*, 349–357 A New Class of HIV–1–Specific 6–Substituted Acyclouridine Derivatives: Synthesis and Anti–HIV–1 Activity of 5– or 6–Substituted Analogues of 1–[(2–Hydroxyethoxy)methyl]–6–(phenylthio)thymine(HEPT).

Tanaka, H. et al., "Synthesis of a Potential Photoaffinity Labeling Reagent for HIV–1 reverse Transcriptase", *Chemical Abstracts*, vol. 120, No. 17, p. 1160 (Apr. 25, 1994).

Tantillo, C. et al., 1994, *J Mol Biol, 243*, 369–387 Locations of Anti–AIDS Drug Binding Sites and Resistance Mutations in the Three–dimensional Structure of HIV–1 Reverse Transcriptase.

Tronchet, JMJ et al., "A QSAR Study Confirming the Heterogeneity of the HEPT Derivative Series Regarding Their Interaction with HIV Reverse Transcriptase", *Eur. J. Med. Chem.*, vol. 32, pp. 279–299 (1997).

Uckun, F. M. et al., 1998, *Antimicrobial Agents and Chemotherapy, 42*, 383 TXU (Anti–CD7)–Pokeweed Antiviral Protein as a Potent Inhibitor of Human Immunodeficiency Virus.

Uckun, F. et al. "N–[2–(1–Cyclohexenyl)Ethyl]–N'–[2–(5–Bromopyridyl)]–Thiourea and N'–[2–(1–Cyclohexenyl)Ethyl]–N'–[2–(5–Chloropyridyl)]–Thiourea As Potent Inhibitors of Multidrug–Resistant Human Immunodeficiency Virus–1", *Bioorganic & Medicinal Chemistry Letters*, Vol 9 pp. 2721–2726, (1999).

Vig, R. et al., "5–Alkyl–2–[(Methylthiomethyl)Thio]–6–(Benzyl)–Pyrimidin–4–(1H)–Ones as Potent Non–Nucleoside Reverse Transcriptase Inhibitors of S–DABO Series", *Bioorganic & Medicinal Chemistry Letters 8*, pp. 1461–1466 (1998).

Vig, R. et al., 1998, *Bioorganic & Medicinal Chemistry*, 6:1789–1797 Rational Design and Synthesis of Phenethyl–5–bromopyridyl Thiourea Derivatives as Potent Non–nucleoside Inhibitors of HIV Reverse Transcriptase.

Weiner, S.J. et al., 1984, *J. Am. Chem. Soc., 106*, 765–784 A New Force Field for Molecular Mechanical Simulation of Nucleic Acids and Proteins.

Zarling, J. M. et al., 1990, *Nature, 347*, 92–95 Inhibition of HIV replication by pokeweed antiviral targeted to CD4+ cells by monoclonal antibodies.

Zhang, et al., 1996, *Antiviral Chemistry & Chemotherapy*, 7(5):221–229 "Synergistic inhibition of HIV–1 reverse transcriptase and HIV–1 replication by combining trovirdine with AZT, ddI and ddC in vitro".

* cited by examiner

PIPERIDINYLETHYL-, PHENOXYETHYL-, AND β-FLUOROPHENETHYL-SUBSTITUTED THIOUREA COMPOUNDS WITH POTENT ANTI-HIV ACTIVITY

PRIORITY OF INVENTION

This application claims priority of invention under 35 U.S.C. §119(e) from U.S. Provisional application No. 60/251,716, filed Dec. 6, 2000, the disclosure of which is incorporated by reference herein.

FIELD OF THE INVENTION

The present invention relates to methods of using compounds as non-nucleoside inhibitors of reverse transcriptase (RT) that are effective against human immunodeficiency virus (HIV), including mutant strains of HIV, and effective in the treatment of multi-drug resistant HIV infection.

BACKGROUND OF THE INVENTION

Agents currently used to treat HIV infection attempt to block replication of the HIV virus by blocking HIV reverse transcriptase (RT) or by blocking HIV protease. Three categories of anti-retroviral agents in clinical use are nucleoside analogs (such as AZT), protease inhibitors (such as nelfinavir), and the recently introduced non-nucleoside reverse transcriptase inhibitors (NNI), such as nevirapine.

The recent development of potent combination anti-retroviral regimens has significantly improved prognosis for persons with HIV and AIDS. Combination therapies are a significant factor in the dramatic decrease in deaths from AIDS (a decrease in death rate as well as absolute number). The most commonly used combinations include two nucleoside analogs with or without a protease inhibitor.

Nevirapine is currently the only NNI compound, which has been used in combination with AZT and/or protease inhibitors for the treatment of HIV. A new series of effective drug cocktails will most likely involve other NNIs in combination with nucleoside and protease inhibitors as a triple action treatment to combat the growing problem of drug resistance encountered in single drug treatment strategies.

The high replication rate of the virus unfortunately leads to genetic variants (mutants), especially when selective pressure is introduced in the form of drug treatment. These mutants are resistant to the anti-viral agents previously administered to the patient. Switching agents or using combination therapies may decrease or delay resistance, but because viral replication is not completely suppressed in single drug treatment or even with a two-drug combination, drug-resistant viral strains ultimately emerge. Triple drug combinations employing one (or two) nucleoside analogs and two (or one) NNI targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181 C and Y188H. In particular, the Y181 C and K103N mutants may be the most difficult to treat, because they are resistant to most of the known NNI compounds.

Recently, a proposed strategy using a knock-out concentration of NNI demonstrated very promising results. The key idea in this strategy is to administer a high concentration of NNI in the very beginning stages of treatment to reduce the virus to undetectable levels in order to prevent the emergence of drug-resistant strains. The ideal NNI compound for optimal use in this strategy and in a triple action combination must meet three criteria:

1) very low cytotoxicity so it can be applied in high doses;
2) very high potency so it can completely shut down viral replication machinery before the virus has time to develop resistant mutant strains; and
3) robust anti-viral activity against current clinically observed drug resistant mutant strains.

In recent years, structure-based drug design has played an increasingly important role in the development of useful anti-AIDS drugs as seen in the success of HIV protease inhibitor design as disclosed in Deek et al., "HIV-1 Protease Inhibitors", *J. Acquired Immune Defic. Syndr. Res. Human Retrovirus,* 98:145–185 (1997). Rational drug design is most effective when detailed structural information about the protein-inhibitor complex is available, a requirement which can be a limitation for reverse transcriptase.

While qualitative assessments of RT-inhibitor complexes provide helpful information in the absence of crystal structures, a systematic quantitative prediction of inhibitory activity of new compounds based on available structural information remains a challenge as discussed in Kroeger Smith et al., "Molecular Modeling Studies of HIV-1 Reverse Transcriptase Nonnucleoside Inhibitors: Total Energy of Complexation as a Predictor of Drug Placement and Activity", *Protein Science,* 4:2203–2222 (1995).

Further, while qualitative assessments of RT-inhibitor complexes have provided helpful information in the development of non-nucleoside inhibitors (NNIs), NNIs to date fail to provide potent inhibition of RT with minimal cytotoxicity. In addition, NNIs to date fail to effectively inhibit known, drug-resistant strains of HIV.

What is needed in the art is new antiviral drugs, which have the following characteristics: (1) potent inhibition of RT; (2) minimum cytotoxicity; and (3) improved ability to inhibit known, drug-resistant strains of HIV.

SUMMARY OF THE INVENTION

It has been discovered that certain thiourea compounds of the present invention demonstrate improved potent and specific antiviral activity compared to known therapeutic agents. The thiourea compounds of the present invention possess the ability to inhibit replication of RT with minimum cytotoxicity. Further, the thiourea compounds of the present invention possess an improved ability to inhibit known, non-nucleoside resistant and drug-resistant strains of HIV.

In one aspect, the present invention is directed to piperidinylethyl-substituted, phenoxyethyl-substituted, and fluorophenethyl-substituted thiourea compounds, which inhibit non-nucleoside resistant or drug-resistant reverse transcriptase (RT) and which inhibit replication of a retrovirus, such as human immunodeficiency virus-1 (HIV-1).

The present invention is further directed to a method for inhibiting non-nucleoside resistant or drug-resistant reverse transcriptase activity of a retrovirus, such as HIV-1, comprising contacting the retrovirus with a thiourea compound of the present invention. The present invention is also directed to a method for inhibiting replication of a non-nucleoside resistant or drug-resistant retrovirus, such as HIV-1, comprising contacting the retrovirus with a thiourea compound of the present invention. In addition, the present invention is directed to a method for treating a non-nucleoside resistant or drug-resistant retroviral infection in a subject, such as an HIV-1 infection, comprising administering a thiourea compound of the invention to the subject.

These and other features and advantages of the present invention will become apparent after a review of the following detailed description of the disclosed embodiments and the appended claims.

DETAILED DESCRIPTION OF THE INVENTION

It has been discovered unexpectedly that certain substituted thiourea compounds possess increased activity against non-nucleoside resistant or drug-resistant HIV while maintaining low levels of cytotoxicity. As such, these compounds are particularly useful as active agents for antiviral compositions and for methods of treating viral infections such as HIV infections. Further, the compounds exhibit improved inhibition of multi-drug resistant strains of HIV.

Definitions:

All scientific and technical terms used in this application have meanings commonly used in the art unless otherwise specified. As used in this application, the following words or phrases have the meanings specified.

As used herein, a "retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

As used herein, "reverse transcriptase (RT)" refers to an enzyme having activity to effect reverse transcription of retroviral RNA to proviral DNA. One means by which RT activity can be determined is by measuring viral replication. One measure of viral replication is the p24 assay described herein.

As used herein, a compound that "inhibits replication of human immunodeficiency virus (HIV)" means a compound that, when contacted with HIV-1, for example, via HIV-infected cells, effects a reduction in the amount of HIV-1 as compared with untreated control. Inhibition of replication of HIV-1 can be measured by various means known in the art, for example, the p24 assay disclosed herein.

As used herein, a "nonnucleoside inhibitor (NNI)" of HIV reverse-transcriptase (HIV-RT) means a compound, which binds to an allosteric site of HIV-RT, leading to noncompetitive inhibition of HIV-RT activity. Examples of known nonnucleoside inhibitors of HIV-RT include, but are not limited to, tetrahydroimidazobenzodiazepinthiones (TIBO), 1-[(2-hydroxyethoxy)methyl]-6-(phenylthio) thymines (HEPT), bis(heteroaryl)piperazines (BHAP), 2'-5'-bis-O-(tertbutyldimethylsilyl)-3'-spiro-5"-(4"-amino-1", 2"-oxathiole-2", 2"-dioxide) pyrimidines (TSAO), dihydroalkoxybenzyloxopyrimidine (DABO) and phenethylthiazolylthiourea (PETT) analogs.

As used herein, "derivative" means a chemical substance derivable from a parent substance by addition or substitution of components and which maintains the activity of the parent substance.

As used herein, "halogen" includes fluoro, chloro, bromo, and iodo.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid, and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt. It is presumed that all compounds disclosed and/or claimed herein include their pharmaceutically acceptable salt form.

As used herein, "pharmaceutically acceptable carrier" includes any material which, when combined with a compound of the invention, allows the compound to retain biological activity, such as the ability to inhibit RT activity, and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, Chapter 43, 14th Ed., Mack Publishing Col, Easton Pa. 18042, USA).

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

As used herein, "wild-type" refers to the phenotype that is characteristic of the members of a species occurring naturally and contrasting with the phenotype of a mutant. A mutation is an event that results in a mutant phenotype. A mutation comprises an alteration of a DNA and/or RNA sequence relative to wild-type sequence. Alterations in DNA and/or RNA sequence can result in alterations of amino acid sequence. An example of a mutation in an amino acid sequence is the Y181 C mutation in HIV-1 strain A17, in which the tyrosine residue at position 181 of reverse transcriptase is replaced with cysteine. Another example is that of HIV strain RT-MDR, in which valine at position 106 of reverse transcriptase is replaced with alanine.

Compounds For Use In the Present Invention:

Compounds for use in the present invention include piperidinylethyl-substituted, phenoxyyethyl-substituted, and fluorophenethyl-substituted thiourea compounds, which inhibit reverse transcriptase (RT) and which inhibit replication of one or more retroviruses, such as human immunodeficiency virus-1 (HIV-1). Compounds include piperidinylethyl-substituted thiourea compounds as shown in Formula I below; phenoxyethyl-substituted thiourea compounds as shown in Formula II below; and fluorophenethyl-substituted thiourea compounds as shown in Formula III below:

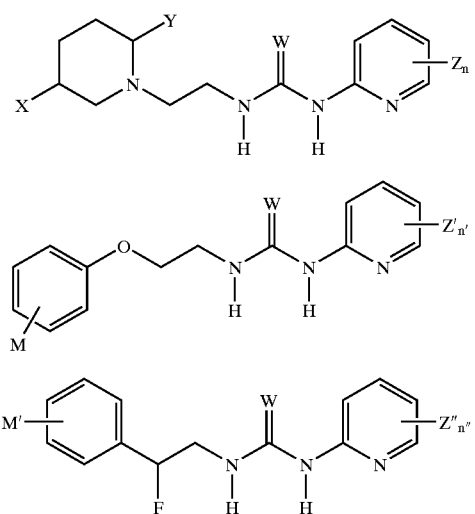

wherein X, Y, Z, Z', and Z" may each independently represent hydrogen, a halogen, or an alkyl group having up to about 6 carbon atoms, wherein at least one of X, Y, Z, Z', and Z" is not hydrogen; W is S or O; M and M' is each independently $CH_3$, $C_2H_5$, F, Cl, Br, I, $NO_2$, CN, $OCH_3$ or $OCH_2CH_3$; and n, n', n" is each independently 0, 1, 2, 3, or 4. Desirably, at least one of X, Y, Z, Z' and Z" is a halogen or a methyl group. More desirably, at least one of X, Y, Z, Z' and Z" is a bromo, a chloro, or a methyl group.

Suitable piperidinyl-substituted thiourea compounds of the present invention include, but are not limited to, compounds of Formula I wherein Z is a halogen or $C_1$–$C_6$ alkyl, and X or Y is a methyl group. Desirably, the piperidinyl-substituted thiourea compound is one of the following: N-[2-(1-piperidinylethyl)]-N'-[2-(5-bromopyridyl)]-thiourea; N-[2-(3-methylpiperidinylethyl)]-N'-[2-(5-bromopyridyl)]-thiourea; N'-[2-(2-methylpiperidinylethyl)]-N'-[2-(5-bromopyridyl)]-thiourea; N-[2-(1-piperidinylethyl)]-N'-[2-(5-chloropyridyl)]-thiourea; or N-[2-(3-methylpiperidinylethyl)]-N'-[2-(5-chloropyridyl)]-thiourea.

It should be noted that the linkage between the piperidine ring and the thiourea component of the compound shown in Formula I can be a propyl linking group instead of the ethyl linking group in Formula I. One suitable compound of the present invention having a propyl linkage is N-[3-(2-methylpiperidinylpropyl)]-N'-[2-(5-chloropyridyl)]-thiourea.

Suitable phenoxyethyl-substituted thiourea compounds of the present invention include, but are not limited to, compounds of Formula II wherein Z' is a halogen or $C_1$–$C_6$ alkyl. Desirably, the phenoxyethyl-substituted thiourea compound is one of the following: N-[2-(phenoxy)ethyl]-N'-[2-(5-chloropyridyl)]thiourea; or N-[2-(phenoxy) ethyl]-N'-[2-(5-bromopyridyl)] thiourea.

Suitable fluorophenethyl-substituted thiourea compounds of the present invention include, but are not limited to, compounds of Formula III wherein Z" is a halogen or $C_1$–$C_6$ alkyl. Desirably, the fluorophenethyl-substituted thiourea compound is one of the following: β-fluoro[2-phenethyl]-N'[2-(5-chloropyridyl)]thiourea; or β-fluoro [2-phenethyl]-N'[2-(5-bromopyridyl)]thiourea.

The piperidinylethyl-substituted, phenoxyyethyl-substituted, and fluorophenethyl-substituted thiourea compounds of the present invention have the ability to inhibit replication of a retrovirus, such as human immunodeficiency virus (HIV). In one embodiment, the thiourea compound inhibits replication of HIV with an $IC_{50}$ of less than 1 μM, as determined by p24 enzyme assay. In a further embodiment, the thiourea compound inhibits replication of HIV with an $IC_{50}$ of less than 0.1 μM. In yet a further embodiment, the thiourea compound inhibits replication of HIV with an $IC_{50}$ of less than 0.01 μM. In even yet a further embodiment, the thiourea compound inhibits replication of HIV with an $IC_{50}$ of less than 0.001 μM.

Compositions For Use In the Present Invention:

One or more of the above-described piperidinylethyl-substituted, phenoxyyethyl-substituted, and fluorophenethyl-substituted thiourea compounds may be combined with an acceptable carrier to form a composition. In one embodiment, the composition is a pharmaceutical composition. Compositions of the present invention are useful for prevention and treatment of retroviral infections, such as HIV infection.

Methods of Using the Compounds of the Invention:

The compounds of the present invention are useful in methods for inhibiting reverse transcriptase activity of a retrovirus. Retroviral reverse transcriptase is inhibited by contacting RT in vitro or in vivo, with an effective inhibitory amount of a compound of the present invention. The compounds of the present invention also inhibit replication of retrovirus, particularly of HIV, such as HIV-1. Viral replication is inhibited, for example, by contacting the virus with an effective inhibitory amount of a compound of the present invention.

The methods of the present invention are useful for inhibiting reverse transcriptase and/or replication of multiple strains of HIV, including mutant strains, and include treating a retroviral infection in a subject, such as an HIV-1 infection, by administering an effective inhibitory amount of a compound or a pharmaceutically acceptable acid addition salt of a compound of Formula I, II, or III. The compound or inhibitor of Formula I, II, or III is preferably administered in combination with a pharmaceutically acceptable carrier, and may be combined with specific delivery agents, including targeting antibodies and/or cytokines. The compound or inhibitor of the present invention may be administered in combination with other antiviral agents, immunomodulators, antibiotics or vaccines.

The compounds of Formula I, II, or III may be administered orally, parentally (including subcutaneous injection, intravenous, intramuscular, intrasternal, or infusion techniques), by inhalation spray, topically, by absorption through a mucous membrane, or rectally, in dosage unit formulations containing conventional non-toxic pharmaceutically acceptable carriers, adjuvants, or vehicles. Pharmaceutical compositions of the present invention may be in the form of suspensions or tablets suitable for oral administration, nasal sprays, creams, sterile injectable preparations, such as sterile injectable aqueous or oleagenous suspensions, or suppositories. In one embodiment, the compounds of the present invention may be applied intravaginally and/or topically, for example in gel form, for prevention of heterosexual transmission of HIV.

For oral administration as a suspension, the compositions may be prepared according to techniques well-known in the art of pharmaceutical formulation. The compositions may contain microcrystalline cellulose for imparting bulk; alginic acid or sodium alginate as a suspending agent; methylcellulose as a viscosity enhancer; and sweeteners or flavoring agents. As immediate release tablets, the compositions may contain microcrystalline cellulose, starch, magnesium stearate and lactose or other excipients, binders, extenders, disintegrants, diluents and lubricants known in the art.

For administration by inhalation or aerosol, the compositions may be prepared according to techniques well-known in the art of pharmaceutical formulation. The compositions may be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions may be formulated according to techniques well-known in the art, using suitable dispersing or wetting and suspending agents, such as sterile oils, including synthetic mono- or diglycerides, and fatty acids, including oleic acid.

For rectal administration as suppositories, the compositions may be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Dosage levels of approximately 0.02 to approximately 10.0 grams of a compound of the present invention per day are useful in the treatment or prevention of retroviral infection, such as HIV infection, AIDS or AIDS-related complex (ARC), with oral doses 2 to 5 times higher. For example, HIV infection may be treated by administration of from about 0.1 to about 100 milligrams of compound per kilogram of body weight from one to four times per day. In one embodiment, dosages of about 100 to about 400 milligrams of a compound are administered orally every six hours to a subject. The specific dosage level and frequency for any particular subject will vary and will depend upon a variety of factors, including, but not limited to, the activity of the specific compound; the metabolic stability and length of action of the compound; the age, body weight, general health, sex, and diet of the subject; the mode of administration; rate of excretion; drug combination; and severity of the particular condition.

The compounds of Formulae I, II, and III may be administered in combination with other agents useful in the treatment of HIV infection, AIDS, or ARC. For example, the compound of the present invention may be administered in combination with effective amounts of an antiviral, immunomodulator, anti-infective, or vaccine. The compound of the present invention may be administered prior to, during, or after a period of actual or potential exposure to retrovirus, such as HIV.

Conjugation to a Targeting Moiety:

Compounds of the present invention can be targeted for delivery to specific cells to be treated by conjugation of the compound to a targeting moiety. Targeting moieties useful for conjugation to the compounds of the present invention include, but are not limited to, antibodies, cytokines, and receptor ligands expressed on the cells to be treated.

Particularly useful targeting moieties for targeting the compounds of the present invention to cells for therapeutic activity include those ligands that bind antigens or receptors present on virus-infected cells to be treated. For example, antigens present on T-cells, such as CD48, may be targeted with antibodies directed against these antigens. Antibody fragments, including single chain fragments, may also be used. Other such ligand-receptor binding pairs are known in the scientific literature for targeting anti-viral treatments to target cells. Methods for producing conjugates of the compounds of the present invention and the targeting moieties are known.

Methods of Making the Thiourea Compounds of the Present Invention:

The piperidinylethyl-substituted and phenoxyyethyl-substituted thiourea compounds of the present invention may be produced as shown in Scheme 1 below.

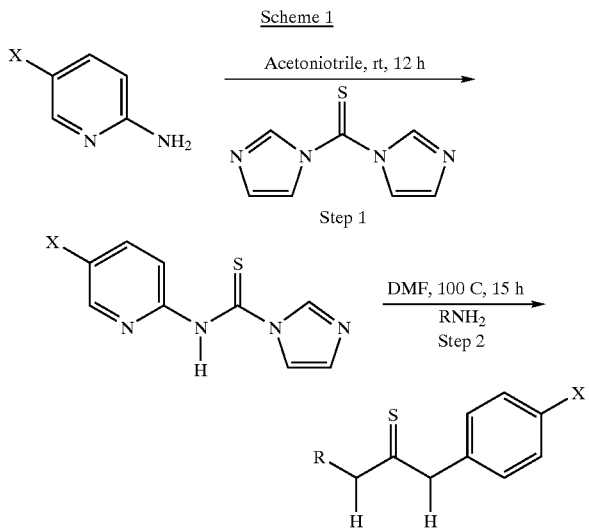

In Step 1 of Scheme 1, a substituted or unsubstituted 2-amino-pyridine is reacted with 1,1'-thiocarbonyldiimidazole in dry acetonitrile under a nitrogen atmosphere. The reaction mixture is stirred at room temperature for about 12 hours. A precipitate forms. The precipitate is filtered, washed with cold acetonitrile, and dried thoroughly under vacuum to yield a pyridinyl-substituted thiocarbonyl intermediate. It should be noted that 1,1'-carbonyldiimidazole can be substituted for 1,1'-thiocarbonyldiimidazole to produce suitable compounds of the invention.

In Step 2 of Scheme 1, the pyridinyl-substituted thiocarbonyl intermediate is added to a dry flask under nitrogen, along with anhydrous dimethylformamide. The contents are stirred for about 30 minutes at room temperature. An appropriately substituted amine, such as 1-(2-aminoethyl)-2-methyl-piperidine, dissolved in dry dimethylformamide is added to the reaction mixture. Suitable piperidinylethyl amines may be prepared by N-alkylation of substituted piperidines using bromoethyl amine.

The reaction mixture is heated to about 110° C. over an oil bath for about 15 hours. The reaction mixture is then cooled and poured into ice water. The contents are stirred for approximately an hour. A precipitate forms. The precipitate is filtered, washed with cold water several times, and dried under vacuum. The precipitate is then added to ethyl acetate, and washed with water and brine. The ethyl acetate layer is separated from the aqueous layer, and subsequently dried over anhydrous sodium sulfate. A filtration step and evaporation of the solvent yields the desired piperidinylethyl-substituted or phenoxyyethyl-substituted thiourea compound. Compounds may be further purified using silica gel column chromatography.

The β-fluorophenethyl-substituted thiourea compounds of the present invention may be produced as shown in Scheme 2 below.

Scheme 2

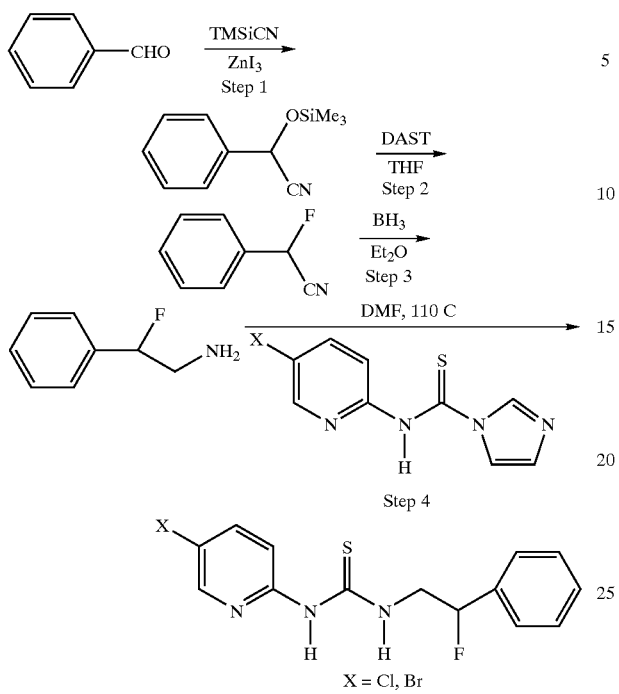

X = Cl, Br

In Step 1 of Scheme 2, benzaldehyde is condensed with trimethyl silyl cyanide (TMSiCN) and zinc iodide ($ZnI_2$) to obtain a cyano hydrin intermediate. In Step 2 of Scheme 2, the cyano hydrin intermediate is reacted with diethylaminosulfur trifluoride (DAST) in tetrahydrofuran (THF) to produce a fluoro-substituted compound, 2-fluoro-2-phenylacetonitrile. In Step 3 of Scheme 2, the fluoro-substituted compound, 2-fluoro-2-phenylacetonitrile, is further reduced using borane in ethyl ether ($Et_2O$) to produce a fluoro-substituted amine.

In Step 4 of Scheme 2, the fluoro-substituted amine produced in Step 3 of Scheme 2 is reacted with an appropriate pyridinyl-substituted thiocarbonyl intermediate as prepared in Step 1 of Scheme 1. It should be noted that an appropriate pyridinyl-substituted carbonyl intermediate can be prepared in Step 1 of Scheme 1 by substituting 1,1'-carbonyldiimidazole for 1,1'-thiocarbonyldiimidazole. The appropriate pyridinyl-substituted carbonyl intermediate can then be used to produce a suitable compounds of Formula III. The fluoro-substituted amine produced in Step 3 of Scheme 2 is condensed with an appropriate pyridinyl-substituted thiocarbonyl intermediate in anhydrous dimethylformamide (DMF) to produce the desired fluoroethyl-substituted thiourea compound. The resulting fluoroethyl-substituted thiourea compound may be further purified using column chromatography.

Proposed Mechanism:

It is believed that the piperidinylethyl-substituted, phenoxyyethyl-substituted, and fluorophenethyl-substituted thiourea compounds of the present invention have the ability to inhibit replication of HIV strains, including multi-drug resistant HIV strains such as Y181 C and V106A, due to their positioning and interaction with sites within the composite NNI-RT binding pocket as previously described in PCT Publication WO 99/47501.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

All chemicals used in the following examples were reagent grade and were purchased from Aldrich Chemical Company (Milwaukee, Wis.) or Sigma Chemical Company (St. Louis, Mo.).

Example 1

Synthesis of Thiourea Compounds of the Present Invention

Ten compounds were synthesized using Scheme 1 as described above. The ten compounds are listed in Table 1 below:

TABLE 1

Thiourea Compounds

| No. | Thiourea Compound |
|---|---|
| 1 | N-[2-(1-piperidinylethyl]-N'-[2-(pyridyl)]-thiourea |
| 2 | N-[2-(1-piperidinylethyl)]-N'-[2-(5-bromopyridyl)]-thiourea |
| 3 | N-[2-(3-methylpiperidinylethyl)]-N'- [2-(5-bromopyridyl)]-thiourea |
| 4 | N'-[2-(2-methylpiperidinylethyl)]-N'[2-(5-bromopyridyl)]-thiourea |
| 5 | N-[2-(1-piperidinylethyl)]-N'-[2-(5-chloropyridyl)]-thiourea |
| 6 | N-[2-(3-methylpiperidinyl ethy1)]-N'-[2-(5-chloropyridyl)]-thiourea |
| 7 | N-[3-(2-methylpiperidinylpropyl)]N'-[2-(5-chloropyridyl)]-thiourea |
| 8 | N-[2-(phenoxy)ethyl]-N'- [2-(pyridyl)]thiourea |
| 9 | N-[2-(phenoxy)ethyl]-N'-[2-(5-chloropyridyl)]thiourea |
| 10 | N-[2-(phenoxy)ethyl]-N'-[2-(5-bromopyridyl)]thiourea |

Synthesis of Piperidinyl-Substituted Compounds 1–7:

Compounds 1–7 were prepared as follows.

Step 1:

Into a 250 ml beaker were added 1,1'-thiocarbonyldiimidazole; substituted (Compounds 2–7) or unsubstituted (Compound 1) 2-amino-pyridine; and 100 ml of dry acetonitrile under a nitrogen atmosphere. (See Table 2 below for the 2-amino-pyridine reactant used to produce each compound). The mixture was stirred at room temperature for about 12 hours. The precipitate was filtered, washed with cold acetonitrile, and dried thoroughly under vacuum to yield a pyridinyl-substituted thiocarbonyl intermediate.

Step 2:

In a subsequent step, the pyridinyl-substituted thiocarbonyl intermediate was added to a dry flask under nitrogen, along with 20 ml of anhydrous dimethylformamide. The contents were stirred for 30 minutes at room temperature. Into this solution was added the appropriate substituted amine, dissolved in 10 ml of dry dimethylformamide. (See Table 2 below for the substituted amine reactant used to produce each compound). The piperidinylethyl amines used in this step were prepared by N-alkylation of substituted piperidines using a bromoethyl amine.

The mixture was heated to 110° C. over an oil bath for about 15 hours. The reaction mixture was cooled and poured into ice water. The contents were then stirred for an additional hour. The precipitate was filtered, washed with cold water several times, and dried under vacuum. The precipitate was then added to ethyl acetate or $CHCl_3$, and washed with water and brine. The separated ethyl acetate or $CHCl_3$ layer was subsequently dried over anhydrous sodium sulfate.

Filtration and evaporation of the solvent yielded the target thiourea compound. Compounds were further purified using silica gel column chromatography.

TABLE 2

Reactants Used to Form Piperidinyl-Substituted Thiourea Compounds

| No. | Step 1-<br>2-amino-pyridine Reactant | Step 2-<br>Substituted Amine Reactant |
|---|---|---|
| 1 | 2-amino-pyridine | 1-(2-aminoethyl)piperidine |
| 2 | 2-amino-5-bromo-pyridine | 1-(2-aminoethyl)piperidine |
| 3 | 2-amino-5-bromo-pyridine | 1-(2-aminoethyl)-3-methyl-piperidine |
| 4 | 2-amino-5-bromo-pyridine | 1-(2-aminoethyl)-2-methyl-piperidine |
| 5 | 2-amino-5-chloro-pyridine | 1-(2-aminoethyl)piperidine |
| 6 | 2-amino-5-chloro-pyridine | 1-(2-aminoethyl)-3-methyl-piperidine |
| 7 | 2-amino-5-chloro-pyridine | 1-(3-aminopropyl)-2-pipecoline |

Synthesis of Phenoxy-Substituted Compounds 8–10:

Compounds 8–10 were prepared as shown in Scheme 1 and as described above with regards to Compounds 1–7. However, the following reactants were used as shown in Table 3 below.

TABLE 3

Reactants Used to Form Phenoxy-Substituted Thiourea Compounds

| No. | Step 1-<br>2-amino-pyridine Reactant | Step 2-<br>Substituted Amine Reactant |
|---|---|---|
| 8 | 2-amino-pyridine | 2-phenoxyethylamine |
| 9 | 2-amino-5-chloro-pyridine | 2-phenoxyethylamine |
| 10 | 2-amino-5-bromo-pyridine | 2-phenoxyethylamine |

Example 2

Synthesis of β-Fluorophenethyl-Substituted Thiourea Compounds of the Present Invention Two compounds were synthesized using Scheme 2 as described above. The two compounds are listed in Table 4 below:

TABLE 4

Fluoroethyl Thiourea Compounds

| No. | Fluoroethyl Thiourea Compound |
|---|---|
| 11 | β-Fluoro[2-phenethyl]-N'[2-(5-chloropyridyl)]thiourea |
| 12 | β-Fluoro[2-phenethyl]-N'[2-(5-bromopyridyl)]thiourea |

Compounds 11 and 12 were prepared as follows. Benzaldehyde was condensed with trimethyl silyl cyanide/zinc iodide to obtain a cyano hydrin compound, which on subsequent reaction with diethylaminosulfur trifluoride (DAST) in tetrahydrofuran (THF) furnished a fluoro-substituted compound, 2-fluoro-2-phenylacetonitrile. This intermediate compound was further reduced using borane in ethyl ether ($Et_2O$) to furnish a fluoro-substituted amine.

The fluoro-substituted amine was then condensed with a halopyridyl-substituted thiocarbimidazole derivative in anhydrous dimethylformamide (DMF) to produce the desired thiourea compound. The appropriate halopyridyl-substituted thiocarbimidazole derivative was prepared as shown in Step 1 of Scheme 1. The resulting compound was further purified by column chromatography.

Example 3

Characterization of Thiourea Compounds of the Present Invention

The physical properties of Compounds 1–12 were determined using techniques as described below.

Proton and carbon nuclear magnetic resonance spectra were recorded on a Varian spectrometer using an automatic broad band probe. All NMR spectra were recorded in $CDCl_3$ or DMSO-$d_6$ at room temperature. The chemical shifts reported are in parts per million relative to DMSO peau, TMS standard. The multiplicity of the signals are designated as follows: s, d, dd, t, q, and m, which correspond to singlet, doublet, doublet of doublet, triplet, quartet, and multiplet respectively. UV spectra were recorded from a Beckmann Model # DU 7400 UV/Vis spectrometer using a cell path length of 1 cm. Fourier Transform Infrared spectra were recorded using an FT-Nicolet model Protege #460 instrument. The infrared spectra of the liquid samples were run as neat liquids using KBr discs. Mass spectrum analysis was conducted using either a Finnigan MAT 95 instrument or a Hewlett-Packard Matrix Assisted Laser Desorption (MALDI) spectrometer model # G2025A. The matrix used in the latter case was cyano hydoxy cinnamic acid. Melting points were determined using a Melt John's apparatus and uncorrected.

Elemental analysis was performed by Atlantic Microlabs (Norcross, Ga.). Column chromatography was performed using silica gel obtained from the Baker Company. The solvents used for elution varied depending on the compound and included one of the following: ethyl acetate, methanol, chloroform, hexane, methylene chloride, and ether.

Characterization data for the synthesized compounds is shown below:

N-[2-(1-piperidinylethyl]-N'-[2-(pyridyl)]-thiourea (1) Yield: 22%; mp: 147–148° C.; UV (MeOH) $\lambda_{max}$: 208, 246, 266, 294 nm; IR: 3219, 3150, 3038, 2938, 1606, 1525, 1475, 769 $cm^{-1}$; $^1$H NMR (DMSO-$d_6$) δ11.88 (s, 1 H), 8.99 (s, 1 H), 8.18 (dd, 1 H, J=5.4, 6.0), 7.63-7.57 (m, 1 H), 6.95-6.90 (m, 1 H), 6.82 (dd, 1 H, J=8.4, 8.2), 3.81 (q, 2 H), 2.59 (t, 2 H), 2.43 (d, 4 H), 2.15 (t, 1 H), 1.62-1.45 (m, 5 H); $^{13}$C NMR(DMSO-$d_6$) δ178.9, 153.5, 146.0, 138.6, 118.0, 112.1, 56.7, 54.5, 43.5, 26.7, 24.8; MALDI-TOF: 265.6.

N-[2-(1-piperidinylethyl)]-N'-[2-(5-bromopyridyl)]-thiourea (2) Yield: 74%; mp 150–152° C.; $^1$H NMR ($CDCl_3$) δ11.53 (br s, 1H), 9.72 (br s, 1H), 8.22 (d, 1H), 7.72-7.68 (dd, 1H, J=9.0,9.0), 6.95-6.92 (d, 1H), 3.84-3.78 (q, 2H), 2.61-2.57 (t, 2H), 2.45 (br s, 4H), 1.64-1.48 (m, 6H); $^{13}$C NMR($CDCl_3$) δ178.1, 151.8, 146.3, 140.8, 113.5, 112.6, 56.1, 54.0, 43.0, 26.3, and 24.3: Anal. calcd for $C_{13}H_{19}BrN_4S$; C, 45.49; H, 5.58; Br, 23.28; N, 16.32; S, 9.34; Found: C, 45.67; H, 5.59; Br, 23.12; N, 16.20; S, 9.36.

N-[2-(3-methylpiperidinylethyl)]-N'-[2-(5-bromopyridyl)]-thiourea (3) Yield: 29%; mp: 115–116° C.; UV ($CHCl_3$) $\lambda_{max}$: 260, 278, 306 nm; IR: 3205, 3153, 3077, 3041, 2927, 2848, 2809, 2763, 1591, 1548, 1519, 1465, 1351, 1303, 1269, 1226, 1189, 1134, 1095, 1004, 973, 864, 825, 756, 572, 509 $cm^{-1}$; $^1$H NMR ($CDCl_3$) δ11.51 (s, 1 H), 9.73 (s, 1 H), 8.20-8.19 (d, 1 H), 7.72-7.68 (dd, 1 H, J=9.0, 9.0), 6.95-6.92 (d, 1 H), 3.84-3.79 (q, 2 H), 2.86-2.81 (t, 2 H), 2.62-2.58 (t, 2 H), 2.02-1.93 (td, 1 H), 1.76-1.49 (m, 6 H), 0.90-0.88 (d, 3 H); $^{13}$C NMR ($CDCl_3$) δ178.2, 151.9, 146.4, 140.9, 113.6, 112.6, 55.9, 53.7, 43.1, 32.9, 31.4, 25.9, 16.7; MALDI-TOF: 358.0 ($C_{14}H_{21}BrN_4S$).

N-[2-(2-methylpiperidinylethyl)]-N'-[2-(5-bromopyridyl)]-thiourea (4) Yield: 11%; mp: 88–89° C.; UV ($CHCl_3$) $\lambda_{max}$: 256, 279, 303 nm; IR: 3203, 3153, 3077, 3041, 2931, 2854, 2798, 1614, 1591, 1567, 1517, 1465, 1363, 1301, 1226, 1093, 1018, 827, 754 $cm^{-1}$; $^1$H NMR ($CDCl_3$) $\delta$11.36 (s, 1 H), 9.47 (s, 1 H), 8.20-8.15 (dd, 1 H, J=15.0, 15.0), 7.64-7.52 (q of d, 1 H), 6.82-6.72 (dd, 1 H, J=24.0, 24.0), 3.83-3.63 (m, 2 H), 2.99-2.81 (m, 3 H), 2.43-2.35 (m, 1 H), 2.15-2.07 (m, 1 H), 1.62-1.42 (m, 3 H), 1.31-1.18 (m, 3 H), 1.03-1.01 (d, 3 H); $^{13}$C NMR ($CDCl_3$) $\delta$178.2, 151.8, 146.4, 140.9, 140.1, 113.5, 55.9, 51.0, 53.3, 38.6, 34.8, 26.2, 23.5, 18.6; MALDI-TOF: 357.3 ($C_{14}H_{21}BrN_4S$).

N-[2-(1-piperidinylethyl)]-N'-[2-(5-chloropyridyl)]-thiourea (5) Yield: 50%; mp: 142–143° C.; UV (MeOH) $\lambda_{max}$: 207, 208, 213, 223, 264, 267, 276 nm; IR: 3215, 3155, 3080, 3020, 2935, 2848, 2763, 1595, 1518, 1471, 1296, 1228, 1184, 1109, 823, 756 $cm^{-1}$; $^1$H NMR (DMSO-$d_6$) $\delta$11.32 (t, 1 H), 10.67 (s, 1 H), 8.13 (d, 1 H, J=2.7), 7.86-7.82 (dd, 1 H, J=8.7, 9.0), 7.18-7.15 (d, 1 H, J=9.0), 3.65-3.59 (q, 2 H), 2.48-2.44 (t, 2 H), 2.35 (s, 4 H), 1.48 (t, 4 H), 1.37 (d, 2 H, J=4.5); $^{13}$C NMR (DMSO-$d_6$) $\delta$178.7, 152.2, 143.5, 138.8, 123.8, 114.1, 56.1, 53.9, 42.4, 26.1, 24.4; MALDI-TOF: 300.6 ($C_{13}H_{19}ClN_4S$+2).

N-[2-(3-methylpiperidinylethyl)]-N'-[2-(5-chloropyridyl)]-thiourea (6) Yield: 26%; mp: 133–134° C.; UV ($CHCl_3$) $\lambda_{max}$: 256, 277, 306 nm; IR: 3209, 3155, 3081, 3043, 2927, 2885, 2809, 2763, 1596, 1550, 1523, 1467, 1321, 1303, 1228, 1191, 1134, 1110, 865, 827, 754, 605 $cm^{-1}$; $^1$H NMR ($CDCl_3$) $\delta$11.52 (s, 1 H), 9.59 (s, 1 H), 8.12-8.11 (d, 1 H), 7.60-7.56 (dd, 1 H, J=9.0, 9.0), 6.97-6.93 (dd, 1 H, J=9.0, 9.0), 3.85-3.79 (q, 2 H), 2.87-2.81 (t, 2 H), 2.62-2.58 (t, 2 H), 1.98-1.97 (td, 1 H), 1.72-1.54 (m, 6 H), 0.90-0.88 (d, 3 H); $^{13}$C NMR ($CDCl_3$) $\delta$178.2, 151.5, 144.2, 138.3, 124.9, 113.1, 61.5, 55.9, 53.6, 43.1, 32.9, 31.5, 25.9, 19.7; MALDI-TOF: 312.9 ($C_{14}H_{21}ClN_4S$).

N-[3-(2-methylpiperidinylpropyl)]-N'-[2-(5-chloropyridyl)]-thiourea (7) Yield: 31%; mp: 117–118° C.; UV (MeOH) $\lambda_{max}$ 207, 255, 275, 304 nm; IR: 3209, 3045, 2931, 2856, 2796, 2219, 1639, 1596, 1531, 1469, 1307, 1228, 1110, 910, 829, 732, 646 $cm^{-1}$; $^1$H NMR ($CDCl_3$) $\delta$11.33 (t, 1 H), 9.62 (s, 1 H), 8.08 (d, 1 H), 7.59-7.55 (dq, 1 H, J=8.7), 6.95-6.92 (d, 1 H, J=8.7), 3.76-3.69 (m, 2 H), 2.87-2.73 (m, 2 H), 2.46-2.37 (m, 1 H), 2.27 (t, 1 H), 2.17-2.09 (td, 1 H), 2.02-1.85 (m, 2 H), 1.48-1.23 (m, 3 H), 1.04 (d, 4 H); $^{13}$C NMR ($CDCl_3$) $\delta$178.7, 151.5, 143.9, 138.4, 125.0, 113.2, 55.8, 52.1, 51.2, 44.0, 34.6, 26.1, 24.8, 23.9, 19.1; MALDI-TOF: 326.8 ($C_{15}H_{23}N_4SCl$), 372.8 (M+2Na).

N-[2-(Phenoxy)ethyl]-N'-[2-(pyridyl)]thiourea (8) Yield: 60%; mp: 168.5–170.5° C.; UV (MeOH) $\lambda_{max}$: 224, 246, 267, 293 nm; IR: 3232, 3045, 2931, 1602, 1560, 1481, 1317, 1245, 1080, 773, 688 $cm^{-1}$; $^1$H NMR (DMSO-$d_6$) $\delta$11.98 (t, 1 H), 10.67 (s, 1 H), 8.17-8.15 (dd. 1 H, J=6.0,6.0), 7.88-7.73 (m, 1 H), 7.31-7.17 (m, 2 H), 7.17-7.14 (dd, 1 H, J=9.0, 6.0), 7.04-6.90 (m, 4 H), 4.19 (t, 2 H), 4.00 (q, 2 H); $^{13}$C NMR (DMSO-$d_6$) $\delta$179.8, 158.2, 153.7, 145.5, 139.0, 129.6, 120.9, 118.0, 114.6, 112.6, 65.7, 44.0; MALDI-TOF: 275.0.

N-[2-(Phenoxy)ethyl]-N'-[2-(5-chloropyridyl)]thiourea (9) Yield: 65%; mp: 168–169° C.; UV (MeOH) $\lambda_{max}$: 245, 265 mn; IR: 3221, 3161, 3088, 3037, 2933, 2875, 1601, 1562, 1533, 1477, 1407, 1359, 1305, 1263, 1238, 1194, 1136, 1111, 1047, 908, 862, 821, 750, 690 $cm^{-1}$; $^1$H NMR (DMSO-$d_6$) $\delta$11.50 (t, 1 H), 10.83 (s, 1 H), 8.19 (d, 1 H, J=2.7), 7.89-7.85 (dd, 1 H, J=9.0, 9.0), 7.28 (q, 2 H), 7.20 (d, 1 H, J=9), 7.00-6.90 (m, 3 H), 4.19 (t, 2 H), 3.99 (q, 2 H); $^{13}$C NMR (DMSO-$d_6$) $\delta$179.6, 158.2, 152.1, 143.8, 138.9, 129.6, 123.9, 120.9, 114.6, 114.2, 65.6, 44.1.

N-[2-(Phenoxy)ethyl]-N'-[2-(5-bromopyridyl)] thiourea (10). Yield: 56%; mp: 162–163° C.; UV (MeOH) $\lambda_{max}$: 249, 268 nm; IR: 3219, 3161, 3084, 3032, 2929, 2875, 1599, 1560, 1527, 1468, 1356, 1307, 1278, 1238, 1191, 1138, 1078, 1047, 1005, 951, 860, 82 1, 752, 690 $cm^{-1}$; $^1$H NMR (DMSO-$d_6$) $\delta$11.48 (t, 1 H), 10.82 (s, 1 H), 8.26 (d, 1 H, J=2.4), 7.97-7.93 (dd, 1 H, J=9, 9.0), 7.27 (q, 2 H), 7.14 (dd, 1 H, J=8.7), 7.00-6.90 (m, 3 H), 4.18 (t, 2 H), 3.99 (q, 2 H); $^{13}$C NMR (DMSO-$d_6$) $\delta$179.6, 158.2, 152.3, 146.0, 141.5, 129.6, 120.9, 114.6, 112.1, 65.6, 44.2.

β-Fluoro[2-phenethyl]-N'-[2-(5-chloropyridyl)] thiourea (11) Yield: 20%; mp: 183–184° C.; UV (MeOH) $\lambda_{max}$: 251, 267 nm; IR: 3224, 3157, 3024, 2925, 2858, 2742, 1822, 1595, 1537, 1477, 1340, 1306, 1197, 1178, 1140, 1093, 1070, 1014, 918, 885, 823, 758, 700 $cm^{-1}$; $^1$H NMR ($CDCl_3$) $\delta$11.63 (bs, 1H), 8.76 (bs, 1H), 8.24-8.23 (d, 1H), 7.76-7.46 (m, 1H), 7.44-7.40 (m, 5H), 6.73-6.70 (m, 1H), 5.94-5.91 (m, ½ H), 5.78-5.74 (m, ½H), 4.57-4.40 (m, 1H), 3.98-3.84 (m, 1H); $^{13}$C NMR ($CDCl_3$) $\delta$179.9, 151.5, 146.6, 141.3, 137.1, 136.9, 128.7, 128.5, 125.4, 125.3, 125.2, 113.5, 113.0, 93.1, 90.8, 51.5*, 51.1*; MALDI-TOF: 311.8 (M+2).

β-Fluoro[2-phenethyl]-N'-[2-(5-bromopyridyl)]thiourea (12) Yield: 37%; mp: 185–186° C.; UV (MeOH) $\lambda_{max}$: 263 nm; IR: 3119, 3161, 3087, 3030, 2924, 1602, 1560, 1533, 1479, 1458, 1340, 1307, 1232, 1178, 1137, 1111, 1012, 916, 855, 868, 825, 758, 700 $cm^{-1}$; $^1$H NMR ($CDCl_3$) $\delta$11.63 (bs,1H), 8.76 (bs,1H), 8.24-8.23 (d, 1H), 7.76-7.46 (m, 1H), 7.44-7.40 (m, 5H), 6.73-6.70 (m,1H), 5.94-5.91 (m, ½ H), 5.78-5.74 (m, ½H), 4.57-4.40 (m, 1H), 3.98-3.84 (m, 1H); $^{13}$C NMR ($CDCl_3$) $\delta$179.9, 151.3, 146.7, 141.3, 137.1, 136.9, 128.8, 128.7, 128.5, 125.4, 125.3, 113.2, 113.1, 93.2, 90.8, 51.6, 51.3; MALDI-TOF: 356.4 (M+2).

Example 4

Ability of Compounds 1-12 To Inhibit Replication of HIV in PBMC Cells

The ability of Compounds 1–12 to inhibit the replication of the HIV-1 strain HTLV$_{IIIB}$ in human peripheral blood mononuclear cells (PBMC) was analyzed using the method described in Uckun et. al., 1998, *Antimicrobial Agents and Chemotherapy* 42:383.

Normal human peripheral blood mononuclear cells (PBMNC) from HIV-negative donors were cultured 72 hours in RPMI 1640 supplemented with 20% (v/v) heat-inactivated fetal bovine serum (FBS), 3% interleukin-2,2 mM L-glutairine, 25 mM HEPES, 2 μL, NAHCO, 50 mg/mL gentamicin, and 4 μg/mL phytohemagglutinin prior to exposure HIV-1 strain HTLV$_{IIIB}$ that was propagated in CCRF-CEM cells. The cells were then infected with virus at a multiplicity of infection (MOI) of 0.1 during a one-hour adsorption period at 37° C. in a humidified 5% CO2 atmosphere. Subsequently, cells were cultured in 96-well microplates (100 μL/well; 2×10$^6$ cells/mL, triplicate wells) in the presence of various inhibitor concentrations. Aliquots of culture supernatants were removed from the wells on the 7$^{th}$ day after infection for p24 antigen enzyme immunoassays (EIA), as previously described in Erice et al., 1993, *Antimicrob. Ag. Chemotherapy* 37:385–838. The applied p24 EIA was the unmodified kinetic assay commercially available from Coulter Corporation/Immunotech, Inc. (Westbrook, Me.).

Compounds 1–12 were also compared to Trovirdine, a known RT inhibitor. The structures of Compounds 1–12 and Trovirdine are given below.

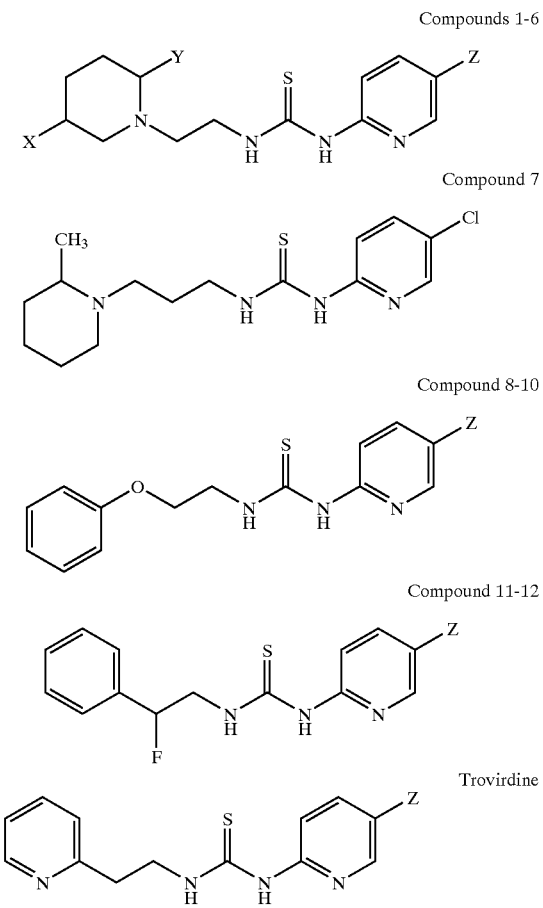

Compounds 1-6

Compound 7

Compound 8-10

Compound 11-12

Trovirdine p24 Assays for Anti-HIV Activity

To test the therapeutic activity of the compounds of the invention, p24 assays were utilized as previously described. (see Erice et.al., 1993, *Antiimicrob. Ag. Chemotherapy* 37:835–838). Normal human peripheral blood mononuclear cells (PBMNC) from HIV-negative donors were cultured 72 hours in RPMI 1640 supplemented with 20%(v/v) heat-inactivated fetal bovine serum (FBS), 3% interleukin-2, 2 mM L-glutairtine, 25 mM HEPES, 2 mmL, NAHCO, 50 mg/mL gentamicin, and 4 mmg/mL phytohemagglutinin prior to exposure to HIV-I at a multiplicity of infection (MOI) of 0.1 during a one-hour adsorption period at 37° C. in a humidified 5% $CO_2$ atmosphere. Subsequently, cells were cultured in 96-well microliter plates (100 mm l/well; $2\times10^6$ cells/mL, triplicate wells) in the presence of various inhibitor concentrations. Aliquots of culture supernatants were removed from the wells on the 7th day after infection for p24 antigen p24 enzyme immunoassays (EIA).

The applied p24 EIA was the unmodified kinetic assay commercially available from Coulter Corporation/Immunotech, Inc. (Westbrooke, Me.), which utilizes a murine monoclonal antibody to HIV core protein coated onto microwell strips to which the antigen present in the test culture supernatant samples binds. Percent inhibition of viral replication was calculated by comparing the p24 values from the test substance treated infected cells with p24 values from untreated infected cells (i.e., virus controls).

In parallel, the effects of various treatments on cell viability were also examined, as described in Enrice et.al., supra. In brief, non-infected PBNWC were treated with each compound for 7 days under identical experimental conditions. A Microculture Tetrazolium Assay (MTA), using 2,3-bis(2-methoxy-4 nitro-5-sulfophenyl)-5-[(phenylarnino)-carbonyl]-2H-tetrazolium hydroxide (XTT), was performed to quantitate cellular proliferation.

$IC_{50}$ values, which represent the concentration required to inhibit by 50% the activity of HIV replication as measured by assays of $HTLV_{IIIB}$ production; cytotoxic concentration ($CC_{50}$); and selectivity index (SI), are reported in the Table below. selectivity index=(IC50/MTA)/(IC50/p24)

TABLE 5

Inhibitory Effects of Compounds 1–12 and Trovirdine on HIV-1 Strain HTL $V_{IIIB}$ in PBMC Cells

| Compound No. | X | Y | Z | $IC_{50}$ [HTL $V_{IIIB}$] µM | CC µM | SI |
|---|---|---|---|---|---|---|
| 1 | H | H | H | >100 | n.d. | n.d. |
| 2 | H | H | Br | 0.002 | n.d. | n.d. |
| 3 | Me | H | Br | 0.08 | n.d. | n.d. |
| 4 (HI-516) | H | Me | Br | <0.001 | 50 | >50,000 |
| 5 | H | H | Cl | 0.001 | n.d. | n.d. |
| 6 | Me | H | Cl | 0.02 | n.d. | n.d. |
| 7 | n.a. | n.a. | n.a. | 0.001 | n.d. | n.d. |
| 8 | n.a. | n.a. | H | 0.005 | 55 | 1,100 |
| 9 | n.a. | n.a. | Cl | 0.004 | >100 | >25,000 |
| 10 | n.a. | n.a. | Br | 0.005 | 92 | 18,400 |
| 11 (HI-566) | n.a. | n.a. | Cl | <0.001 | 30 | >30,000 |
| 12 (HI-565) | n.a. | n.a. | Br | <0.001 | 50 | >50,000 |
| Trovirdine | n.a. | n.a. | n.a. | 0.007 | 100 | 14,286 | n.a. = not applicable.
n.d. = not determined.

As shown in Table 5, the unsubstituted parent pyridyl thiourea compound, N-[2-(1-piperidinylethyl]-N'-[2-(pyridyl)] thiourea (Compound 1), exhibited no anti-HIV activity even at concentrations of greater than 100 µM. In contrast, halopyridyl thiourea derivatives (Compounds 2 and 5) inhibited HIV-1 replication at nanomolar concentrations. The heterocyclic derivative (Compound 2) was more potent than Trovirdine and abrogated HIV replication at nanomolar concentrations.

Compounds 1–5 exhibited promising anti-HIV activity with 100% inhibition at concentrations of greater than or equal to 1 µM. Introduction of a single methyl functional group on the piperidine ring significantly altered the potency of these compounds. While methyl substitution at the 3-position of the piperidine ring reduced the activity (Compound 3), methyl substitution at the 2-position enhanced the activity (Compound 4).

The $IC_{50}$ value of Compound 4, N-[2-(2-methylpiperidinylethyl)]-N'-[2-(5-bromopyridyl)] thiourea, was less than 0.001 µM. Along with Compound 4, the fluoro thiourea compounds (Compounds 11 and 12) were the most potent compounds, inhibited HIV-1 replication in PBMC with subnanomolar $IC_{50}$ values, as well as, selectivity indices of greater than 30,000.

As shown in Table 5, Compounds 4, 11 and 12 were more than 4–5 fold more active in inhibiting HIV-1 replication compared to the phenoxyethyl thiourea compounds (Compounds 9 and 10). Further, Trovirdine, which lacks the fluoro substitution on the ethyl linker group, was greater than 7-fold less active than Compounds 11 ands 12. The $IC_{50}[HTLV_{IIIB}]$ value for trovirdine was 0.007 µM versus <0.001 µM for Compounds 11 and 12.

Example 5

Ability of Select Compounds To Inhibit Replication of NNI-Resistant HIV-1 Strains The ability of Compounds 4 (HI-516), 11 (HI-566), and 12 (HI-565) to inhibit the replication of NNI-resistant HIV-1 strains, A17 (Y181C) and RT-MDR (V106A), was analyzed. The anti-HIV activity of the compounds was measured by determining their ability to inhibit the replication of HIV-1 strains A17 in PBMC from healthy volunteer donors and RT-MDR in H9 cells.

Compounds 4, 11, and 12 were compared with nevirapine or delavirdine, two known non-nucleoside reverse transcriptase inhibitors of HIV-1 RT. The results are given in Table 6 below.

TABLE 6

Inhibitory Effects of Compounds 4, 11, and 12, Nevirapine and Delavirdine on NM-Resistant HIV-1 Strains

| | $IC_{50}$ ($\mu$M) | |
|---|---|---|
| Compound | RT-MDR (V106A) | A17 (Y181C) |
| 4 (HI-516) | 1.9 | >100 |
| 11 (HI-566) | 0.1 | 0.1 |
| 12 (HI-565) | 0.2 | 0.1 |
| Nevirapine | 1.4 | 21.4 |
| Delavirdine | 0.4 | 50.0 |

As shown in Table 6, both Compounds 11 and 12 inhibited the multidrug resistant HIV-1 strain RT-MDR with submicromolar $IC_{50}$ values. Compound 11 (HI-566) was 14-fold more potent than nevirapine and 4-fold more potent than delavirdine. Compound 12 was 7-fold more potent than nevirapine and 2-fold more potent than delavirdine. Both compounds inhibited the Y181C mutant HIV-1 strain A17 with an $IC_{50}$ value of 0.1 $\mu$M. Compounds 11 and 12 were 200-fold more potent than nevirapine ($IC_{50}$=21.4 $\mu$M) and 500-fold more potent than delavirdine ($IC_{50}$=50.0 $\mu$M). Unlike Compounds 11 and 12, Compound 4 was not active against A17 and was less active than nevirapine or delavirdine against RT-MDR.

This application contains reference to numerous patents and publications, each of which is hereby incorporated by reference as if fully set forth. While a detailed description of the present invention has been provided above, the present invention is not limited thereto. The present invention described herein may be modified to include alternative embodiments, as will be apparent to those skilled in the art. All such alternatives should be considered within the spirit and scope of the present invention, as claimed below.

What is claimed is:

1. A method comprising administering to a patient an effective multidrug-drug resistant HIV treating dose of a compound having the formula:

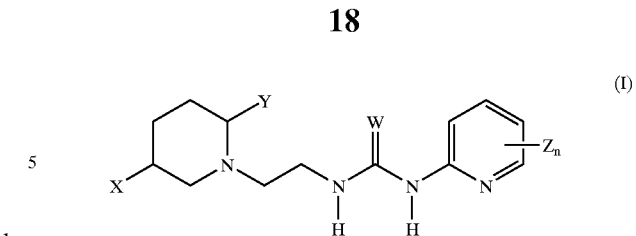

wherein X, Y, and Z may each independently represent hydrogen, F, Cl, I, or an alkyl group having up to about 6 carbon atoms; and wherein at least one of X or Y is not hydrogen; W is S or O; and n is independently 1, 2, 3, or 4.

2. The method of claim 1, wherein Z is a halogen, and X or Y is a methyl group.

3. The method of claim 1, wherein the compound comprises:

N-[2-(3-methylpiperidinylethyl)]-N'-[2-(5-bromopyridyl)]-thiourea;

N'-[2-(2-methylpiperidinylethyl)]-N'-[2-(5-bromopyridyl)]-thiourea; or

N-[2-(3-methylpiperidinylethyl)]-N'-[2-(5-chloropyridyl)]-thiourea.

4. A method comprising administering to a patient an effective multidrug-drug resistant HIV treating dose of a compound selected from the group:

N-[2-(3-methylpiperidinylethyl)]-N'-[2-(5-bromopyridyl)]-thiourea;

N'-[2-(2-methylpiperidinylethyl)]-N'-[2-(5-bromopyridyl)]-thiourea;

N-[2-(3-methylpiperidinylethyl)]-N'-[2-(5-chloropyridyl)]-thiourea; and

N-[3-(2-methylpiperidinylpropyl)]-N'-[2-(5-chloropyridyl)]-thiourea.

5. A method comprising contacting cells infected with multidrug-drug resistant HIV with an NM-resistant or multidrug-drug resistant HIV reverse transcriptase inhibiting amount of a compound selected from the group:

N-[2-(3-methylpiperidinylethyl)]-N'-[2-(5-bromopyridyl)]-thiourea;

N'-[2-(2-methylpiperidinylethyl)]-N'-[2-(5-bromopyridyl)]-thiourea;

N-[2-(3-methylpiperidinylethyl)]-N'-[2-(5-chloropyridyl)]-thiourea; and

N-[3-(2-methylpiperidinylpropyl)]-N'-[2-(5-chloropyridyl)]-thiourea.

6. The method of claim 5, wherein the compound inhibits replication of HIV with an $IC_{50}$ of less than 1 $\mu$M, as determined by p24 enzyme immunoassay.

7. The method of claim 6, wherein the compound inhibits replication of HIV with an $IC_{50}$ of less than 0.1 $\mu$M, as determined by p24 enzyme immunoassay.

8. The method of claim 7, wherein the compound inhibits replication of HIV with an $IC_{50}$ of less than 0.01 $\mu$M, as determined by p24 enzyme immunoassay.

9. The method of claim 8, wherein the compound inhibits replication of HIV with an $IC_{50}$ of less than 0.001 $\mu$M, as determined by p24 enzyme immunoassay.

10. A compound of the formula:

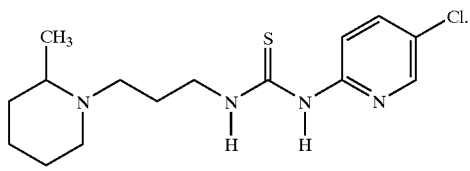

11. A pharmaceutical composition comprising a therapeutically effective amount of the compound of claim 10 and a pharmaceutically acceptable carrier or diluent.

12. A method for inhibiting HIV reverse transcriptase comprising contacting said HIV with an effective inhibitory amount of a compound of claim 10.

13. A method for treating HIV infection in a subject comprising administering to said subject an anti-HIV effective amount of a compound of claim 10.

* * * * *